United States Patent [19]

Martin

[11] Patent Number: 4,986,298

[45] Date of Patent: Jan. 22, 1991

[54] VACUUM REGULATOR WITH ANTIBINDING VALVE STEM CONNECTOR ASSEMBLY AND METHOD

[75] Inventor: Gordon D. Martin, Buffalo Grove, Ill.

[73] Assignee: Aeros Instruments, Inc., Northbrook, Ill.

[21] Appl. No.: 444,867

[22] Filed: Dec. 4, 1989

[51] Int. Cl.⁵ .................................... G05D 16/06
[52] U.S. Cl. ................................ 137/15; 137/505.13; 137/907; 251/86
[58] Field of Search .................... 137/505, 494, 505.26, 137/505.27, 505.29, 15, 315, 907, 509, 505.13, 505.42; 251/86

[56] References Cited

U.S. PATENT DOCUMENTS

| | | | |
|---|---|---|---|
| 1,273,304 | 7/1918 | Yates | 251/86 X |
| 1,620,322 | 3/1927 | Browne . | |
| 1,927,972 | 9/1933 | Young | 137/907 X |
| 2,318,157 | 5/1943 | Heiser | 137/907 X |
| 3,305,207 | 2/1967 | Calderoni et al. | 251/86 |
| 3,474,822 | 10/1969 | Kuhn et al. | 251/86 X |
| 4,137,992 | 2/1979 | O'Neil . | |
| 4,238,991 | 12/1980 | Pickles | 92/85 A |
| 4,513,785 | 4/1985 | Kenny | 137/881 |
| 4,836,241 | 6/1989 | Schoenwald | 137/907 X |
| 4,903,726 | 2/1990 | Martin et al. | 137/505.13 |

Primary Examiner—Stephen M. Hepperle
Attorney, Agent, or Firm—Potthast & Ring

[57] ABSTRACT

A medical vacuum regulator (10) with a vacuum regulation chamber (20, 34) connected with a supply of unregulated vacuum (26) through a regulation control valve seat opening (24A) controlled by means of a valve head (28, 28A) at one end of a valve stem (30) extending through a valve stem guide (32) and coupled at its opposite end to a movable wall (36, 38) of the regulation chamber (20, 34) is provided with an antibinding valve stem connector assembly (12) comprising a ball and socket connector (46, 48) respectively coupled to the valve stem (30) and the movable wall (36, 38) to enable relative movement between the valve stem guide (32) and valve stem (30).

23 Claims, 1 Drawing Sheet

VACUUM REGULATOR WITH ANTIBINDING VALVE STEM CONNECTOR ASSEMBLY AND METHOD

BACKGROUND OF THE INVENTION

This invention relates to a vacuum regulator, such as the type used to regulate vacuum pressure of a medical regulating vacuum controller to control the applicaiton of vacuum pressure for drawing bodily fluids from a patient, and more particularly, to such a vacuum regulator having a valve stem carried by a movable wall of a regulation chamber.

In various medical applications vacuum pressure controllers are employed to control the level of vacuum pressure applied to draw bodily fluids from a patient. Such controllers have a housing within which is contained a vacuum pressure meter, an inlet port for connection with a supply of vacuum pressure, a nonregulated or line vacuum chamber in open communication with the inlet port, a regulation vacuum chamber with a valve opening for controlled communication with the line vacuum chamber and with an outlet port for connection of regulated vacuum pressure to the patient.

The vacuum regulation chamber includes a well within which is slideably received a vacuum regulating cartridge. The cartridge carries a movably mounted valve head at the end of a valve stem for mating engagement with a valve seat of the valve opening in the well. The carriage body is mounted for sliding receipt of a projecting valve guide portion thereof within the well in response to relative rotation of a knob to selectively move the valve head to different positions relative to the valve seat. These different positions correspond to different vacuum levels selected from a range of different vacuum pressures.

In known cartridges, the cartridge body contains therewithin a moving wall of the regulation chamber in the form of a bellows-like apparatus or other flexible diaphragm to which one end of the valve stem is attached. The moving wall responds to decreases in pressure in the well to move the valve head closer to the valve opening to decrease the effective valve opening and thereby increase the pressure in the well. Likewise, when the vacuum decreases in the well, the bellows respond by moving the valve head away from the valve seat to increase the vacuum. In this way the vacuum which appears at the outlet port and provided to the patient is regulated relative to the line vacuum.

The valve stem extends from the one end attached to the movable wall within the cartridge body through the valve stem portion of the cartridge body within the well to the valve head outside the cartridge body but within the well. Specifically, the valve stem extends through an elongate passageway through the valve stem guide portion.

A problem which has been encountered with this arrangement is that binding can occur between the valve stem and the elongate guide passageway through which it extends. When such binding occurs, it causes an erratic relationship between the adjustment of the knob and the resultant outlet vacuum level achieved thereby. This, in turn, causes accurate adjustment of the vacuum level to be both difficult to achieve and unreliable.

SUMMARY OF THE INVENTION

It is therefore an object of the present invention to provide a vacuum regulator of the general type having a moving wall for controlling movement of a valve stem extending through a valve guide which reduces binding and thereby enhances easy and reliable adjustment of regulated vacuum pressure and a method of making such a regulator.

It has been discovered that a major cause of binding between the valve stem and the valve stem guide, or guide passageway, has been angular misalignment between the valve stem guide and the valve stem. While this problem can be alleviated to the extent that exact alignment can be achieved during mass production, reliably accurate alignment to the degree of precision required is difficult to achieve during mass production and can greatly add to the cost of the cartridge because of quality control rejects and field returns. Moreover, even if accurate alignment is achieved during initial production, variations in material thickness of the flexible movable wall, other variations in material and general wear and tear can over time cause angular misalignment and binding after a course of successful binding free operation.

This binding problem is overcome in accordance with the present invention by provision of a vacuum regulator of the type described above with an antibinding valve stem connector assembly which permits relative movement of the stem relative to the moving wall in response to self-alignment forces and a method of making same which eliminates the need for exacting alignment.

Specifically, it is the object to provide such an antibinding valve stem connector assembly in a vacuum regulator having a body with a vacuum regulation chamber connectable with a supply of unregulated line vacuum through a regulation control valve seat opening controlled by means of a valve head carried at one end of a valve stem extending through a valve stem guide and coupled at its opposite end to a movable wall of the regulation chamber, in the form of a first connector carried by the movable wall for coupling the opposite end of the valve stem thereto for movement relative thereto and a second connector carried by the valve stem at said opposite end for movable mating connection with the first connector, said first and second connectors enabling movement of said valve stem in response to self-aligning forces imposed thereon by said valve stem guide to align it with the valve stem guide.

It is also an object of providing a method of making a vacuum regulator with a valve stem having a valve head at one end and a body extending through a valve guide to an opposite end coupled to a movable wall of a vacuum regulation chamber by means of which binding of the stem with the valve guide is reduced without requiring the high cost of precision in production. The method comprises the steps of providing a first movable valve stem connector to the opposite end of the valve stem, passing the valve stem through the valve stem guide, mounting a mating movable valve stem connector to the movable wall, positioning the movable wall to approximately align the mating movable valve stem connector opposite the valve stem guide and securing the movable wall in position after said step of positioning. The mating movable valve stem connectors are interconnected to enable movement of the valve stem relative to the valve stem guide in the event of minor misalignment which would cause binding between the valve stem guide and the valve stem.

BRIEF DESCRIPTION OF THE DRAWINGS

The foregoing objects, features and advantages will be described in greater detail and other advantageous features will be made apparent from the following detailed description of the preferred embodiment given in reference to the figures of the drawing, in which.

DETAILED DESCRIPTION

Figure 1:
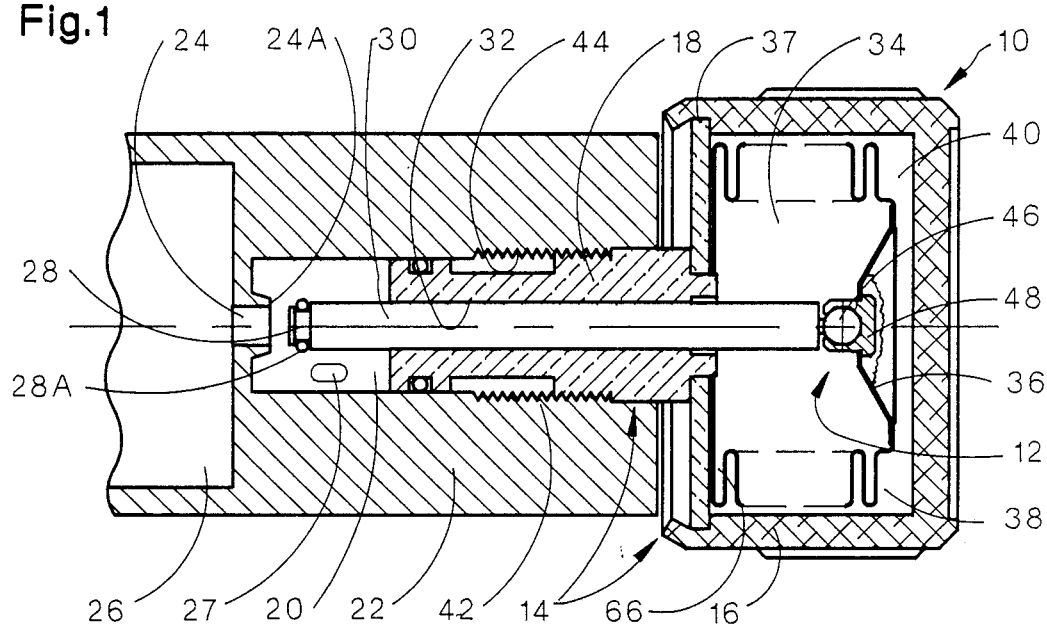
FIG. 1 is an enlarged cross-sectional side view of the preferred embodiment of the vacuum regulator of the present invention.

Referring now to FIG. 1, the preferred embodiment of the vacuum regulator 10 of the present invention is seen to include a number of known parts of vacuum regulators which cooperate with each other to achieve vacuum regulation as described above in addition to antibinding valve stem connector assembly 12.

These known parts include a cartridge 14 having a generally cylindrical, hollow knob section 16 and a relatively narrow, centrally, axially aligned valve stem guide portion 18 projecting outwardly therefrom which fits into a cylindrical well 20 within a wall 22. The well has an inlet port 24 which is in communication with a source of unregulated vacuum pressure within an unregulated vacuum chamber 26. The connection of the vacuum in the unregulated vacuum chamber 26 and the well is controlled by means of a valve head 28 including an annular O-ring 28A which mates against an annular valve seat 24A of the inlet port 24 to regulate the pressure in the well. Connection of the regulated vacuum to a patient is via a regulated vacuum outlet port 27 in the well 20.

The valve head 28 is mounted at a free end of an elongate valve stem 30 which slideably extends through an elongate, cylindrical valve guide passageway, or valve guide, 32 into a regulation cavity 34. In the regulation cavity 34, the opposite end of the valve stem 30 is attached to a movable wall 36 of a bellows-like or other, flexible, air impermeable diaphragm 38. There is sufficient clearance between the inner wall of the valve guide passageway 32 and the valve stem for free communication between the well 20 and the valve regulation cavity 34 for them together to comprise a single vacuum regulation chamber.

The diaphragm 38 preferably has a bellows-like configuration so that it will automatically, resiliently return to its unflexed state in which the valve head 28 is spaced from the valve seat 24A. In such case, the diaphragm itself functions to bias the valve head 28 to move toward an open position, i.e. toward the right of FIG. 1. Alternatively, if other than a resilient bellows is used, a spiral spring or the like is used to provide this bias.

A space 40 on the other side of the movable wall 36 but within the hollow knob section 16 is vented at 37 to atmosphere. Accordingly, whenever the vacuum in the regulation cavity 34 is reduced by vacuum becoming in open communication with cavity 34 through inlet port 24, the movable wall 36 moves in a direction to increase the volume of the regulation cavity 34 to increase the vacuum. At the same time, the valve stem is carried by the movable wall 36 and slides away from the inlet port to decrease the seal of the valve head O-ring 28A and the valve seat 24A between the unregulated vacuum chamber 26 and the well 20. This further increases the vacuum therein and thus in the vacuum regulation cavity 34. When the vacuum in the regulation cavity 34 is increased the reverse occurs: the wall 36 moves to reduce the volume and decrease the vacuum which moves the valve head 28 toward the valve seat 24A to increase the seal which also decreases the vacuum.

Gross regulation of vacuum is achieved by rotating the hollow knob section 16 to advance a threaded section 42 of the protruding stem guide portion 18 through an internally threaded portion 44 of well 20 and thus move the entire cartridge 14, including the valve head 28, either closer or further away from the valve seat 24. In the position shown, the vacuum in the well 20 is unregulated, but under normal operation, the knob is rotated sufficiently to cause the O-ring 28A to be pressed against the valve seat 24A. The tighter the pressure against the valve seat 24A, the lower the regulated vacuum level in the well 20 being provided to the patient through outlet port 27.

As discussed above, a problem with known vacuum regulators of this general type arise when the valve stem 30 binds within the valve stem guide, or passageway, 32 rather than sliding smoothly therewithin. It has been discovered that this binding is caused in great part by angular misalignment of the valve stem guide 32 and the valve stem 30.

In accordance with the present invention, this misalignment and thus the binding problems caused thereby are reduced through provision of the antibinding valve stem connector assembly 12 which enables movement of the valve stem in response to binding forces to maintain proper alignment and reduce the binding. Preferably the movement which is enabled is pivotal movement relative to the moving wall 36.

Figure 2:
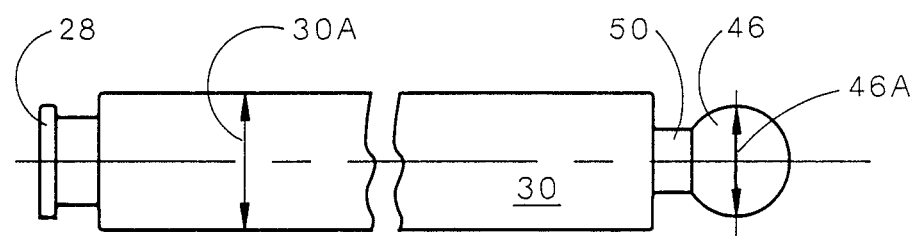
FIG. 2 is an enlarged view of the valve stem of FIG. 1 with a preferred embodiment of a movable connector of the present invention carried at one end thereof.
Figure 3A:
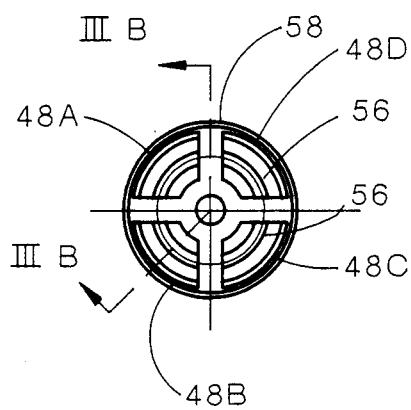
FIG. 3A is an enlarged plan view of the mating movable connector of the present invention as attached to the movable wall of FIG. 1.
Figure 3B:
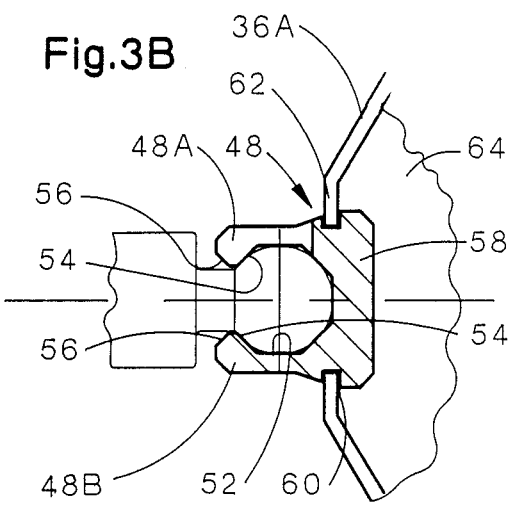
FIG. 3B is a sectional view of the connector taken along section line IIIB—IIIB of FIG. 3A.

In the preferred embodiment, the antibinding valve stem assembly includes a first movable connector in the form of a socket connector, or socket 48, as best seen in FIGS. 3A and 3B which mates with a second movable connector in the form of a ball connector, or ball, 46 carried at the end of valve stem 30, as best seen in FIG. 2. This ball and socket connection enables universal pivotal movement of the valve stem 30 relative to the movable wall 36 in response to binding forces imposed by the valve stem guide 32 to realign the valve stem 30 to reduce or eliminate such binding.

Referring specifically to FIG. 2, the ball 46 is preferably integrally formed at the end of the valve stem 30 opposite the free end with the valve head 28. Preferably, the ball 46 has a diameter 46A which is not greater than a diameter 46 of the valve stem 30 to enable the valve stem 30 and ball 30A to pass through the valve guide passageway 32 with the ball 46 leading. The ball 46 is connected to the end of valve stem 30 by means of a relatively narrow, cylindrical neck 50. As seen in FIG. 1 and illustrated in broken line in greater detail in FIG. 3B, fingers of the socket connector 48 encircle and resiliently close around said neck 50 to maintain the ball 46 in mating connection with the socket connector 48.

Referring to FIGS. 3A and 3B, the socket connector 48 is seen to have four substantially identical arcuate fingers 48A, 48B, 48C and 48D which define a socket 52 within which the ball 46 is received. Each of the fingers, 48A-D has an inwardly extending surface 54 which wraps around the portion of the ball 46 and the neck 50 to hold the ball against longitudinal movement out of the socket.

Preferably, each of the fingers 48A-D also has a beveled cam surface 56. These cam surfaces 56 are engaged by the forward end of the ball 46 as it is pushed toward the socket 52 to spread apart the resilient fingers for a snap-fit insertion of the ball 46 into the socket 52. After the ball 46 is fully inserted, the fingers resiliently return to the position shown in FIG. 3B with the fingers secured around the neck. The surfaces 54 are used as cam surfaces to spread the fingers when the ball 46 is pulled apart from the socket connector 48 in the event of maintenance or repairs after initial assembly.

The fingers 48A-D are connected at their fixed ends to a cylindrical base 58 with an annular shoulder 60 pressed against the peripheral edges 62 of a mating circular hole in the movable wall 36. The fingers 48A-D are inserted through the hole until edges 62 bear against shoulder 60 and then the base 58 is secured against separation from the movable wall 36 by a layer of adhesive 64, such as epoxy, which covers the back of the base 58 between a conical wall section 36A of the movable wall 36. Preferably, epoxy adhesive 66 is also used to secure the end of the bellows side section 38 of the movable wall 36.

According to the preferred method of making a vacuum regulator like the regulator 10 of FIG. 1 to reduce binding, a first movable connector such as ball 46, is mated to the end of a value stem, such as valve stem 30, at the end opposite the valve head 28. The valve stem 30 is passed through the valve stem guide, and the first movable connector is attached to a mating second movable connector such as socket connector 48. The movable wall 36 is positioned to allign the mating socket connector 48 opposite the valve stem guide, but in keeping with this invention such alignment can be made only approximately and need not be done with perfect precision. After the movable wall 36 is positioned in approximate alignment, it is secured in said position, such as by adhesive 66. The movable valve stem connectors then enable movement of the valve stem 30 relative to the valve stem guide 32 in the event of any misalignment which would cause binding between the valve stem guide 32 and the valve stem 30. Preferably, the connectors are attached to each other by snap fasteners after the valve stem 30 and the ball connector 46 are both passed through the valve stem guide 32 after the movable wall 36 has been approproximately alligned and secured in position.

While a particular embodiment has been disclosed herein, the invention is not limited to the precise details. For instance, although the preferred movement of the valve stem 30 is pivotal, connectors which employ translational movement of the valve stem relative to the movable wall 36 are also contemplated. Reference should therefore be made to the appended claims which define the scope of the invention.

I claim:

1. In a vacuum regulator having a body with a vacuum regulation chamber connectable with a supply of unregulated line vacuum through a regulation control valve seat opening controlled by means of a valve head carried at one end of a valve stem extending through a valve stem guide and coupled at its opposite end to a movable wall of the regulation chamber, said valve stem reciprocating within the valve guide during normal regulating operation, the improvement being an antibinding valve stem connector assembly, comprising:
   a first connector carried by the movable wall for coupling the opposite end of the valve stem to the movable wall for movement of the valve stem relative thereto; and
   a second connector carried by the valve stem at said opposite end for movable mating connection with the first connector, said first and second connectors enabling movement of said valve stem in response to self-aligning forces imposed thereon by said valve stem guide to align the valve stem with the valve stem guide during normal regulating operation thereof.

2. The vacuum regulator of claim 1 in which said relative movement is pivotal movement between said first and second connectors.

3. The vacuum regulator of claim 2 in which said pivotal movement is substantially universal pivotal movement.

4. The vacuum regulator of claim 1 in which one of said first and second connectors is a ball connector and the other is a mating socket connector.

5. The vacuum regulator of claim 4 in which one of said first and second connector comprises a socket member with a socket defined by a plurality of fingers.

6. The vacuum regulator of claim 5 in which said fingers have beveled ends defining cam surfaces engageable by a ball of the ball connector for spreading apart the fingers as the ball is pushed toward the socket to receive the ball within said socket.

7. The vacuum regulator of claim 5 in which said ball connector has a ball receivable within the socket and a relatively narrowed neck portion interconnecting the ball and the end of the valve stem about which said fingers are closed after the ball is inserted into the socket.

8. The vacuum regulator of claim 4 in which said first connector is a socket connector and the second connector is a ball connector.

9. The vacuum regulator of claim 8 in which
   said second connector includes a ball, and the valve stem has a preselected diameter which is not less than that of the ball to enable the valve stem to be passed through the valve stem guide leading with the opposite end.

10. The vacuum regulator of claim 1 in which said valve stem guide includes a cylindrical passageway through which the valve stem extends and which has a center axis approximately aligned with said first connector.

11. The vacuum regulator of claim 1 in which both said valve stem and valve guide are elongate.

12. The vacuum regulator of claim 1 in which said first connector has a base with a peripheral shoulder integrally formed therewith for engagement by the periphery of an opening in the movable wall.

13. The vacuum regulator of claim 12 including a layer of adhesive overlying the base to secure the shoulder against separation from the periphery of the opening.

14. The vacuum regulator of claim 12 including a connector element integrally formed with and extending away from said base and shoulder of the first connector through the opening in the movable wall for coupling with said second connector.

15. A method of making a vacuum regulator with a valve stem having a valve head at one end and a body extending through a valve guide to an opposite end coupled to a movable wall of a vacuum regulation chamber by means of which binding of the stem with the valve guide is reduced, comprising the steps of:

providing a movable valve stem connector at the opposite end of the valve stem;

passing the valve stem through the valve stem guide;

mounting a mating movable valve stem connector to the movable wall;

positioning the movable wall to approximately align the mating movable valve stem connector opposite the valve stem guide;

securing the movable wall in position after said step of positioning; and interconnecting the mating movable valve stem connectors, said movable valve stem connectors enabling movement of the valve stem relative to the valve stem guide in the event of minor misalignment which would cause binding between the valve stem guide and the valve stem during normal regulating operation.

16. The method of claim 15 in which
said step of passing is performed after said step of mounting, and
both said movable valve stem connector and said valve stem are passed through said valve stem guide.

17. The method of claim 15 in which said step of attaching is achieved by the step of snap fastening the mating movable connectors together for movement relative to each other.

18. The method of claim 15 in which said step of mounting is performed after said step of passing.

19. The method of claim 15 including the step of securing the mating movable valve stem connector to the movable wall at a fixed position before said step of positioning.

20. The method of claim 15 in which said first and second connectors are pivotal connectors to enable pivotal movement of the valve stem to adjust in response to misalignment forces during normal regulating operation.

21. The method of claim 20 in which said first and second pivotal connectors are mating universal pivotal connectors.

22. The method of claim 15 in which said movable valve stem connector is a ball connector and said mating movable valve stem connector is a mating socket connector.

23. The method of claim 15 in which said step of mounting includes the step of resiliently forcing said ball connector into mating engagement with the socket connector.

* * * * *